United States Patent [19]

Green et al.

[11] 4,398,014
[45] Aug. 9, 1983

[54] SULFOXONIUM SALTS AND THEIR USE AS POLYMERIZATION CATALYSTS

[75] Inventors: George E. Green, Stapleford; Edward Irving, Burwell; Bernard P. Stark, Great Shelford, all of England

[73] Assignee: Ciba-Geigy Corporation, Ardsley, N.Y.

[21] Appl. No.: 314,275

[22] Filed: Oct. 23, 1981

[30] Foreign Application Priority Data

Nov. 4, 1980 [GB] United Kingdom ............... 8035382

[51] Int. Cl.³ .................................................. C08F 2/50
[52] U.S. Cl. ................................. 528/89; 528/90; 528/138; 528/139; 528/141; 528/143; 528/233; 528/236; 528/240; 528/242; 528/361; 528/408; 528/409; 526/192; 526/193; 526/195; 526/220; 526/225; 204/159.21; 204/159.24
[58] Field of Search ............... 526/192, 193, 195, 220, 526/225; 528/89, 90, 138, 139, 141, 143, 233, 236, 240, 242, 361, 408, 409; 204/159.21, 159.24; 568/30, 32

[56] References Cited

U.S. PATENT DOCUMENTS

| | | |
|---|---|---|
| 3,196,184 | 7/1965 | Berry . |
| 3,442,901 | 5/1969 | Koenig et al. . |
| 3,708,296 | 1/1973 | Schlesinger . |
| 3,984,357 | 10/1976 | Koshar ............................... 260/2 R |
| 3,989,644 | 11/1976 | Bolon et al. . |
| 4,032,673 | 6/1977 | Schroeter et al. . |
| 4,058,400 | 11/1977 | Crivello . |
| 4,058,401 | 11/1977 | Crivello . |
| 4,069,054 | 1/1978 | Smith . |
| 4,081,276 | 3/1978 | Crivello . |
| 4,085,019 | 4/1978 | Green . |
| 4,090,936 | 5/1978 | Barton . |
| 4,101,513 | 7/1978 | Fox et al. . |
| 4,102,687 | 7/1978 | Crivello . |
| 4,105,806 | 8/1978 | Watt . |
| 4,108,747 | 8/1978 | Crivello . |
| 4,113,895 | 9/1978 | Watt et al. . |
| 4,136,102 | 1/1979 | Crivello . |
| 4,138,255 | 2/1979 | Crivello . |
| 4,139,385 | 2/1979 | Crivello . |
| 4,154,872 | 5/1979 | Tsao et al. . |
| 4,156,035 | 5/1979 | Tsao et al. . |
| 4,156,046 | 5/1979 | Lien et al. . |
| 4,161,405 | 7/1979 | Crivello . |
| 4,161,478 | 7/1979 | Crivello . |
| 4,173,476 | 11/1979 | Smith et al. . |
| 4,186,108 | 1/1980 | Carlson et al. . |
| 4,193,799 | 3/1980 | Crivello . |
| 4,197,174 | 4/1980 | Chang . |
| 4,201,640 | 5/1980 | Watt . |
| 4,210,703 | 7/1980 | Scantlin et al. . |
| 4,216,288 | 5/1980 | Crivello . |
| 4,218,531 | 8/1980 | Carlson . |
| 4,227,978 | 10/1980 | Barton . |
| 4,230,814 | 10/1980 | Crivello . |
| 4,231,886 | 11/1980 | Carlson . |
| 4,233,421 | 11/1980 | Worm . |
| 4,238,619 | 12/1980 | Crivello et al. . |
| 4,241,204 | 12/1980 | Crivello . |
| 4,250,006 | 2/1981 | Guarney et al. . |
| 4,250,053 | 2/1981 | Smith . |
| 4,250,203 | 2/1981 | Schlesinger et al. . |
| 4,299,938 | 11/1981 | Green et al. ...................... 526/192 |
| 4,339,567 | 7/1982 | Green et al. ...................... 528/102 |

FOREIGN PATENT DOCUMENTS

2833648 2/1979 Fed. Rep. of Germany .
1526923 10/1978 United Kingdom .
1565671 2/1980 United Kingdom .

OTHER PUBLICATIONS

E. J. Corey et al., J. Am. Chem. Soc. 84, 867 (1962).
W. E. Truce et al., Tetrahedron Ltrs., 1966, 3681.

*Primary Examiner*—Joseph L. Schofer
*Assistant Examiner*—Bernard Lipman
*Attorney, Agent, or Firm*—Luther A. R. Hall

[57] ABSTRACT

New aromatic sulfonylsulfoxonium salts are of formula

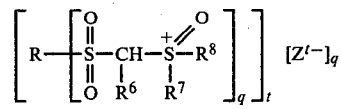

where
q is 1 to 4,
R denotes an aliphatic, cycloaliphatic, or aromatic group,
$R^6$ denotes H, an alkyl or aralkyl group, or a group $-COR^9$, $-CO-NH-(CO)_r-R^{10}$, or $-SO_2-R^{11}$, where r is zero or 1,
one, but not both, of R and $R^6$ denoting an aromatic group,
$R^7$ denotes an alkyl, alkenyl, cycloalkyl, cycloalkylalkyl, or aralkyl group,
$R^8$ has the same meaning as $R^7$ but may alternatively represent a dialkylamino group or, if $R^7$ denotes alkyl, it may alternatively represent an arylamino group,
$R^9$, $R^{10}$, and $R^{11}$ each denote an alkyl, aryl, or aralkyl radical of 1 to 25 carbon atoms,
t is 1, 2, or 3, and
$Z^-$ denotes a t-valent anion of a protic acid.

The salts, e.g., dimethyl-p-toluenesulfonylmethylsufoxonium hexafluorophosphate, are useful as catalysts for the polymerization of cationically polymerizable materials by means of actinic radiation and/or heat. Polyepoxides and resols may be photopolymerized in the presence of the salts and subsequently crosslinked with a latent heat-curing agent.

14 Claims, No Drawings

SULFOXONIUM SALTS AND THEIR USE AS POLYMERIZATION CATALYSTS

BACKGROUND OF THE INVENTION

This invention relates to sulphoxonium salts and to compositions comprising a cationically-polymerisable material and a sulphoxonium salt. It also relates to the polymerisation of such compositions by means of actinic radiation and to the optional further crosslinking of photopolymerised products so obtained by means of heat in the presence of heat-curing agents, to the polymerisation of such compositions by the effect of heat alone, and to the use of the compositions as surface coatings, in printing plates, in printed circuits, and in reinforced composites, and as adhesives.

For a number of reasons, it has become desirable to induce polymerisation of organic materials by means of actinic radiation. Employing photopolymerisation procedures may, for example, avoid the use of organic solvents with their attendant risks of toxicity, flammability, and pollution, and the cost of recovering the solvent. Photopolymerisation enables insolubilisation of the resin composition to be restricted to defined areas, i.e., those which have been irradiated, and so permits the production of printed circuits and printing plates or allows the bonding of substrates to be confined to required zones. Further, in production processes, irradiation procedures are often more rapid than those involving heating and a consequential cooling step.

It has been known for some years that certain aromatic diazonium salts undergo decomposition on exposure to actinic radiation and that, if the salt is mixed with a cationically-polymerisable substance, then the Lewis Acid which is generated in situ on irradiation induces polymerisation (see, for example, British Pat. No. 1,321,263). However, the diazonium salts are not entirely satisfactory: the pot-life of the mixture of diazonium salt and cationically-polymerisable substance is often too short, particularly in daylight, and secondly, nitrogen is generated during liberation of the Lewis Acid catalyst, which evolution of gas restricts the range of processes in which the catalysts may successfully be employed.

Numerous proposals have therefore been made for the replacement of these diazonium salts by others which, while liberating an acid catalyst on irradiaton, do not also evolve nitrogen: particularly intensively studied have been onium salts of sulphur, and iodonium salts.

Thus, it has recently been disclosed, in British Pat. No. 1,516,511 and its United States equivalent, U.S. Pat. No. 4,058,401, that a mono-1,2-epoxide, an epoxide resin (i.e., a substance containing on average more than one 1,2-epoxide group), or a mixture thereof, may be polymerised or cured by means of a radiation-sensitive aromatic onium salt of oxygen, sulphur, selenium, or tellurium present in an amount capable of effecting the polymerisation or cure of the epoxide (or polyepoxide) by release of a Bronsted Acid catalyst when exposed to radiant energy. The only such salts described in the specification are of the formula

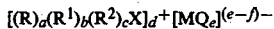   I where
R denotes a monovalent aromatic radical,
$R^1$ denotes an alkyl, cycloalkyl, or substituted alkyl group,
$R^2$ denotes a polyvalent aliphatic or aromatic radical forming a heterocyclic or fused ring structure,
X denotes oxygen, sulphur, selenium, or tellurium,
M denotes an atom of a metal or metalloid, such as antimony, iron, tin, bismuth, aluminum, gallium, indium, titanium, zirconium, scandium, vanadium, chromium, manganese, boron, phosphorus, or arsenic,
Q denotes a halogen radical,
a denotes 0, 1, 2, or 3,
b denotes 0, 1, or 2,
c denotes 0 or 1, the sum of a+b+c being 3 or the valency of X,
d denotes (e−f),
f is the valency of M, and is an integer of from 2 to 7, and
e is more than f and is an integer of up to 8.

Shortly afterwards, in British Pat. No. 1,518,141, and also in its corresponding U.S. Pat. No. 4,058,400, the same patentee disclosed that monomeric or prepolymeric, cationically polymerisable organic materials free from and 1,2-epoxide group, selected from vinyl monomers, vinyl prepolymers, cyclic ethers, cyclic esters, cyclic sulphides, cyclic amines, and organosilicon cyclics, can also be polymerised by exposing them to radiant energy in the presence of an effective amount of a radiation-sensitive onium salt of the Group VIA elements listed above. The only onium salts described are likewise of formula I above.

Still more recently, in its U.S. Pat. No. 4,102,687, the same patentee disclosed that the curing of urea-formaldehyde resins, melamine-formaldehyde resins, and phenolformaldehyde resins could be initiated by exposing them to ultraviolet radiation in the presence of a Group VIA onium salt, curing being completed by heating. Again, only the onium salts of formula I are mentioned.

Subsequent disclosures of this patentee concerning onium salts of sulphur have been confined to sulphonium salts.

Thus, British Pat. No. 1,535,492 describes the use of radiation-sensitive sulphonium salts of arylsulphonic, haloarylsulphonic, alkylsulphonic, and haloalkylsulphonic acids for the cationic polymerisation of epoxide resins, vinyl monomers and prepolymers, cyclic organic ethers, cyclic organic esters, cyclic organic sulphides, cyclic amines, and cyclic organic silicon compounds.

Its U.S. Pat. No. 4,139,385 discloses the use of sulphonium and other salts in the curing of polyolefins by means of polythiols. A polyethylenically unsaturated compound, such as diallyl phthalate, diallyl maleate, or triallyl cyanurate, is mixed with a polythiol, such as trimethylolpropane trithioglycollate or pentaerythitol tetra(3-mercaptopropionate) and, e.g., triphenylsulphonium hexafluoroarsenate or tetrafluoroborate, and then exposed to ultraviolet light. The salts used as catalysts are all of the formula

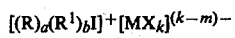   II

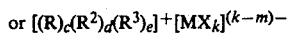   III

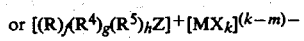   IV where
R denotes a monovalent aromatic radical,

R¹ denotes a divalent aromatic radical,

R² denotes a polyvalent aliphatic or aromatic radical forming a heterocyclic or fused ring structure, R⁴ denotes an alkyl, alkoxy, cycloalkyl, or substituted alkyl radical, R⁵ denotes a polyvalent radical forming an aromatic, heterocyclic or fused ring structure, M denotes an atom of a metal or a metalloid, X denotes a halogen radical, Z denotes a nitrogen, phosphorus, arsenic, bismuth, or antimony atom, a denotes 0 or 2, b denotes 0 or 1, where a+b=2 or the valency of iodine, c denotes 0 or 3, d denotes 0 or 2, e denotes 0 or 1, such that (c+d+e)=3 or the valency of sulphur, f is an integer of from 0 to 4, g is 0, 1, or 2, h is 0, 1, or 2, such that (f+g+h)=4 or the valency of Z, j is k−m, m is the valency of M, being 2 to 7, and k is an integer of more than 1 but not more than 8.

Its West German Offenlegungsschrift No. 2 833 648 discloses that triarylsulphonium salts of formula

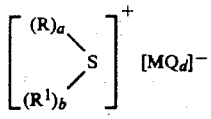 V can be used to initiate the curing, on irradiation, of an aliphatically-unsaturated composition containing a 1,2-epoxide group, such as glycidyl acrylate, or a mixture of an epoxide resin with an aliphatically-unsaturated substance such as methyl methacrylate, a polyester, or styrene. In formula V, R denotes an aromatic hydrocarbon or heterocyclic group of 6 to 13 carbon atoms, which may be substituted, R¹ denotes a divalent aromatic hydrocarbon or heterocyclic group, which may be substituted, a is 1 or 3, b is 0 or 1, S has a valency of 3, which may be satisfied by R alone or by a combination of R and R¹, M denotes an atom of a metal or metalloid, Q denotes a halogen radical, and d is 4, 5, or 6.

Its U.S. Pat. No. 4,136,102 describes various sulphonium salts containing a hexafluorophosphate, hexafluoroarsenate, or hexafluoroantimonate anion and their use in curing epoxide resins. They are stated to be also useful for the polymerisation of a variety of unspecified cyclic organic and cyclic organo-silicon compounds.

Its West German Offenlegungsschrift No. 2 730 725 discloses the photo-induced curing, by means of aromatic onium salts, of epoxide resin compositions which also contain a polyvinyl acetal. The only onium salts of sulphur indicated are those of formula I.

Its U.S. Pat. No. 4,081,276 describes a process for the formation of photoresist images, especially for printed circuit production, wherein a layer of a photoinitiator is exposed to radiant energy and then contacted with a cationically polymerisable material, e.g., an epoxide resin. Again, the only onium salts of sulphur cited are those of formula I above.

Another patentee has described, in Belgian Pat. No. 845 746, the photopolymerisation, using as catalyst an aromatic sulphonium salt or an aromatic iodonium salt, of mixtures comprising a compound having an epoxide functionality of more than 1.5 epoxide groups per molecule and a compound having hydroxy functionality of at least one.

This second patentee describes, in U.S. Pat. No. 4,090,936, photohardenable liquid compositions comprising (a) an organic compound having an average epoxide functionality in the range of about 1 to 1.3, (b) from about 3 to 50% by weight, calculated on the weight of (a), of an organic polymer which is compatible with (a) and has a glass transition temperature in the range of about −20° C. to 105° C., being a polymer derived from at least one acrylate or methacrylate monomer, or a copolymer of styrene and allyl alcohol, or a polyvinyl butyral polymer, and (c) an aromatic complex salt photoinitiator which is an onium salt of a Group VA or Group VIA element or a halonium salt. The only onium salts of sulphur indicated are sulphonium salts.

Another disclosure of this second patentee, U.S. Pat. No. 4,069,054, relates to photopolymerisable compositions containing a cationically polymerisable monomer, an aromatic sulphonium compound, and an aromatic tertiary amine, aromatic tertiary diamine, or an aromatic polycyclic compound as a sensitiser.

An aromatic sulphonium salt, namely triphenylsulphonium hexafluorophosphate, has been used commercially for the photopolymerisation of epoxide resins.

We have now surprisingly found that cationically polymerisable materials can be polymerised by means of actinic radiation or heat in the presence of certain aromatic sulphonylsulphoxonium salts as catalysts.

Unlike compositions of the prior art containing sulphonium salts as catalysts, compositions of this invention do not liberate obnoxious mercaptan odours on irradiation.

We have further found that, contrary to what would be expected from the teachings of U.S. Pat. No. 4,102,687, urea-formaldehyde resins may be cured on irradiation in the presence of an aromatic sulphonylsulphoxonium salt of this invention without the need to apply heat.

SUMMARY OF THE INVENTION

This invention accordingly provides an aromatic sulphonylsulphoxonium salt of the formula

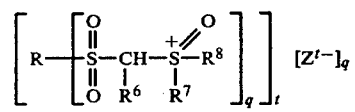 VI where q is an integer of from 1 to 4,

R denotes an aliphatic, cycloaliphatic, or aromatic group of valency q, having from 1 to 25 carbon atoms and being directly linked through a carbon atom thereof to the sulphur atom of the indicated adjacent sulphonyl group, $R^6$ denotes a hydrogen atom, an alkyl or aralkyl group of 1 to 25 carbon atoms, an acyl group of formula —$COR^9$ or a group of formula $$-CO-NH-(CO)_r-R^{10} \qquad \text{VII}$$

or

   VIII one, but not both, of R and $R^6$ denoting an aromatic group having from 4 to 25 carbon atoms, $R^7$ denotes an alkyl group of 1 to 12 carbon atoms, an alkenyl group of 2 to 4 carbon atoms, a cycloalkyl group of 3 to 8 carbon atoms, a cycloalkylalkyl group of 4 to 10 carbon atoms, an aryl group of 4 to 24 carbon atoms, or an aralkyl group of 5 to 16 carbon atoms, $R^8$ has the same meaning as $R^7$ but may alternatively represent a dialkylamino group of 2 to 6 carbon atoms or, if $R^7$ denotes a said alkyl group, it may alternatively represent an arylamino group of 4 to 8 carbon atoms, $R^9$ denotes an alkyl, aryl, or aralkyl radical of 1 to 25 carbon atoms, directly linked through a carbon atom thereof to the indicated —CO— group, r is zero or 1, $R^{10}$ denotes an alkyl, aryl, or aralkyl radical of 1 to 25 carbon atoms, directly linked through a carbon atom thereof to, if r denotes zero, the indicated nitrogen atom, or if r denotes 1, the carbon atom of the indicated adjacent carbonyl group, $R^{11}$ denotes an alkyl, aryl, or aralkyl radical of 1 to 25 carbon atoms, directly linked through a carbon atom thereof to the indicated sulphur atom, t represents 1, 2, or 3, and $Z^{t-}$ denotes a t-valent anion of a protic acid, preferably of an inorganic acid.

Another aspect of this invention provides compositions comprising (a) a compound, or mixture of compounds, capable of being transformed into a higher molecular weight-material under the influence of a cationic catalyst, and (b) an aromatic sulphonylsulphoxonium salt of this invention.

A further aspect of this invention provides a process for the transformation into a higher molecular weight-material of a compound, or mixture of compounds, capable of being converted into a higher molecular weight-material under the influence of a cationic catalyst, comprising subjecting said compound or said mixture to actinic radiation and/or heat in the presence of an aromatic sulphonylsulphoxonium salt of this invention.

DESCRIPTION OF THE PREFERRED EMBODIMENTS

In Formula VI, R may denote, for example, an aliphatic radical of 1 to 8 carbon atoms, especially, when R is monovalent, an alkyl or alkenyl radical of 1 to 6 carbon atoms or, when R is polyvalent, an alkenylene or alkylene radical of 1 to 6 carbon atoms, said alkyl, alkenyl, alkylene or alkenylene radical optionally being substituted by from one to three chlorine, fluorine or bromine atoms or interrupted in the chain by an ether oxygen atom.

R may alternatively denote an aromatic group of 4 to 25 carbon atoms, which may be a homocyclic or heterocyclic aromatic group. By "heterocyclic aromatic group" is meant an aromatic group in which at least one —$CH_2$— or —CH= group of a ring of an aromatic compound is replaced by an atom other than carbon, usually nitrogen, oxygen, or sulphur. Examples of heterocyclic aromatic groups are 2-furyl and 2-pyridyl groups. Preferably, R denotes a homocyclic aromatic group of 6 to 25 carbon atoms, for example a tricyclic group such as an anthryl, phenanthryl, or fluorenyl group, or an anthrylene, phenanthrylene, or fluorenylene group. More preferably it represents (i) a monocyclic or dicyclic aryl or aralkyl group of 6 to 16 carbon atoms, particularly a phenyl, a 2-phenylethyl, a benzyl, or a naphthyl group, or a group of formula

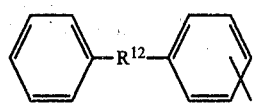   IX where $R^{12}$ denotes a carbon-carbon bond, an ether oxygen atom, or a group of formula —$CH_2$— or —$C(CH_3)_2$—, (ii) a monocyclic or dicyclic arylene or aralkylene group of 6 to 16 carbon atoms, particularly a phenylene, a phenylenemethylene (—$C_6H_4CH_2$—), a xylylene, or a naphthylene group, or a group of formula

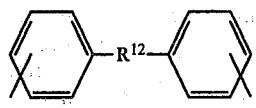   X where $R^{12}$ has the meaning assigned in formula IX, which aryl, aralkyl, arylene, or aralkylene groups may be substituted in the aromatic ring or rings by one to three chlorine, fluorine, or bromine atoms, or by one to three alkyl groups each of 1 to 4 carbon atoms, or by one to three alkoxy groups, each of 1 to 4 carbon atoms.

Specific examples of suitable groups R are phenyl, p-chlorophenyl, 3,4-dichlorophenyl, o-tolyl, p-tolyl, p-methoxyphenyl, 2,4-toluylene, 2,6-toluylene, benzyl, 2-phenylethyl, o-, m-, and p-phenylene, p-phenylenemethylene, and methylenebis(phenylene).

$R^7$ and $R^8$ are preferably each an alkyl group of 1 to 4 carbon atoms or a phenyl or a naphthyl group which may be substituted in the aromatic ring or rings by one or two alkyl groups, each of 1 to 4 carbon atoms, or by one or two alkoxy groups, each of 1 to 4 carbon atoms, or by one or two fluorine, chlorine, or bromine atoms. Most preferably they are each a methyl group.

Where R denotes an aromatic group, $R^9$, $R^{10}$, and $R^{11}$ may each be an aliphatic, cycloaliphatic or aromatic group. Where R denotes an aliphatic or cycloaliphatic group, $R^9$, $R^{10}$, and $R^{11}$ each denote an aromatic group. $R^9$, $R^{10}$, and $R^{11}$ may, for example, have the same meaning as R where R represents a monovalent group. Preferably, R denotes an aromatic group and $R^9$, $R^{10}$, and $R^{11}$ each denote an aliphatic radical of 1 to 8 carbon atoms, especially an alkyl or alkenyl radical of 1 to 6 carbon atoms which may be substituted by from one to three chlorine, fluorine, or bromine atoms or interrupted in the chain by an ether oxygen atom.

Specific examples of suitable groups $R^9$, $R^{10}$, and $R^{11}$ are methyl, ethyl, and 2-ethoxyethyl groups.

As indicated above, if R is not an aromatic group then $R^6$ must be one, in which case it is an aralkyl group, preferably of 6 to 16 carbon atoms, an aracyl radical, preferably of 6 to 10 carbon atoms, an aralkacyl radical, preferably of 7 to 17 carbon atoms, a arylaminocarbonyl group, preferably of 6 to 10 carbon atoms, an aralkylaminocarbonyl group, preferably of 7 to 11 carbon atoms, an aracylaminocarbonyl groups, preferably of 6 to 16 carbon atoms, or an aralkacylaminocarbonyl group, preferably of 7 to 17 carbon atoms, or an arylsulphonyl group, preferably of 6 to 10 carbon atoms, or an aralkylsulphonyl group, preferably of 7 to 11 carbon atoms.

$Z^{t-}$ is the anion of an acid capable of bringing about the polymerisation of a cationically-polymerisable material. It may denote, for example, $CH_3SO_4^-$, but it preferably denotes $Cl^-$, $Br^-$, $NO_3^-$, $HSO_4^-$, $HSO_3^-$, $ClO_4^-$, $CF_3SO_3^-$, $CF_3COO^-$, $CH_3C_6H_4SO_3^-$, $H_2PO_4^-$, $SO_4^{--}$, $PO_4^{---}$, or an anion of formula $$MX_n^- \qquad \qquad XI$$

where

M denotes an atom of a metal or of a metalloid,

X denotes a halogen atom, preferably of fluorine or of chlorine, and n is 4, 5, or 6, and is one more than the valency of M, or $$SbF_5(OH)- \qquad \qquad XII$$

M preferably denotes an atom of boron or bismuth, and more especially antimony, arsenic, or phosphorus. The anion or anions $MX_n^-$ may thus be, for example, $BiCl_6^-$ or $BF_4^-$, but most preferably $MX_n^-$ represents $PF_6^-$, $SbF_6^-$, or $AsF_6^-$.

The sulphoxonium salts of formula VI may be prepared as follows:

A. In the first stage a sulphonyl fluoride of formula $$R(SO_2F)_q \qquad \qquad XIII$$

is reacted with 2q molar proportions of an oxosulphonium ylide of formula

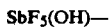
$$\qquad \qquad XIV$$

to give a sulphonyl-containing ylide of formula

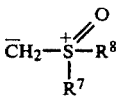
$$\qquad \qquad XV$$

Oxosulphonium ylides of formula XIV are accessible from sulphoxonium chlorides of formula

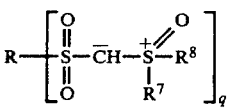
$$\qquad \qquad XVI$$

by treatment with strong bases such as sodium hydride (E. J. Corey and M. Chaykovsky, J. Amer. Chem. Soc., 1962, 84, 867). Reaction of such ylides with alkyl, aryl and aralkyl sulphonyl fluorides is described by W. E. Truce and G. D. Madding, Tetrahedron Letters, 1966, 3681-3687.

B. In the second stage an ylide of formula XV is converted into a sulphoxonium salt of formula VI by one of the following procedures:

1. Sulphoxonium salts of formula VI where $R^6$ denotes a hydrogen atom may be obtained by neutralisation of an ylide of formula XV with q/t molar proportions of a protic acid of formula $H_tZ$, e.g., hydrochloric, nitric, phosphoric, tetrafluoroboric, or hexafluorophosphoric acid.

2. Sulphoxonium salts of formula VI where $R^6$ denotes an alkyl or aralkyl group may be obtained by reaction of an ylide of formula XV with an alkylating agent, for example an alkyl or aralkyl halide, followed by neutralisation with q/t molar proportions of a protic acid of formula $H_tZ$.

3. Sulphoxonium salts of formula VI where $R^6$ denotes a group of formula $-COR^9$ may be obtained by reaction of an ylide of formula XV with an acylating agent to introduce a group of formula $-COR^9$, e.g., an acyl chloride, followed by neutralisation with q/t molar proportions of a protic acid of formula $H_tZ$.

4. Sulphoxonium salts of formula VI where $R^6$ denotes a group of formula VII and r denotes zero or 1 may be obtained by reaction of an ylide of formula XV with an isocyanate of formula $R^{10}(CO)_rNCO$, followed by neutralisation with q/t molar proportions of a protic acid of formula $H_tZ$.

5. Those where $R^6$ denotes a group of formula VIII may be obtained by reaction of an ylide of formula XV with an equimolar proportion of a sulphonyl fluoride of formula $R^{11}SO_2F$ to afford the sulphonyl oxosulphonium ylide of formula XVII

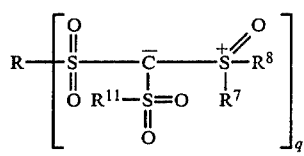
$$\qquad \qquad XVII$$

followed by neutralisation with q/t molar proportions of a protic acid of formula $H_tZ$.

Sulphoxonium salts of formula VI where $R^6$ denotes an alkyl or aralkyl group, an acyl group of formula $-COR^9$, or a group of formula VII, may alternatively be prepared by reacting an oxosulphonium ylide of formula XIV with an alkylating agent, acylating agent or an isocyanate respectively, reacting 2q molar proportions of the resulting ylide with a sulphonyl fluoride of formula XIII, using the method described by Truce and Madding, loc. cit., to give a sulphonyl-containing ylide and neutralising the latter with q/t molar proportions of a protic acid of formula $H_tZ$.

The reaction of oxosulphonium ylides with alkylating agents, acylating agents and isocyanates is described in U.S. Pat. No. 3,442,901.

Where a particular protic acid of formula $H_tZ$ is not available, or is difficult to handle, salts such as hexafluorophosphates and hexafluoroantimonates may be made by double decomposition of the corresponding chlorides or other suitable salts. For example, dimethyltoluenesulphonylmethylsulphoxonium hexafluorophosphate may be obtained by precipitation on adding an aqueous solution of potassium hexafluorophosphate to an aqueous solution of dimethyltoluenesulphonylmethylsulphoxonium chloride. The corresponding hexafluoroantimonate may be made by addition of solid potassium hexafluoroantimonate to the aqueous solution of the chloride: if the potassium hexafluoroantimonate is first dissolved in water then, due to hydrolysis, the product isolated is the hydroxopentafluoroantimonate ($Z'^- = SbF_5(OH)^-$).

Specific examples of suitable sulphonylsulphoxonium salts are dimethyl-p-toluenesulphonylmethylsulphoxonium hexafluorophosphate, and the corresponding hexafluoroantimonate, dimethylphenylsulphonylmethylsulphoxonium hexafluorophosphate, and tris(-dimethyl-p-toluenesulphonylmethylsulphoxonium) orthophosphate.

In the compositions of this invention, the amount of (b) employed is sufficient to induce polymerisation of (a) on exposure of the composition to actinic radiation or on heating it. Usually, from 0.1 to 7.5, especially from 0.5 to 6, parts by weight of (b) are employed per 100 parts by weight of component (a).

Component (a) may be, for example, an oxetane, a thi-irane, or a tetrahydrofuran. Preferably it is a 1,2-epoxide, a vinyl monomer or prepolymer, an aminoplast, or a phenoplast.

When it is a 1,2-epoxide, $Z'^-$ in formula VI must represent $CF_3SO_3-$, a group of formula $MX^-_n$ as aforesaid or a group of formula $SbF_5OH^-$. Suitable mono-1,2-epoxides include epichlorohydrin, propylene oxide, glycidyl ethers of a monohydric alcohol or phenol, such as n-butyl glycidyl ether or a phenyl glycidyl ether, and glycidyl esters such as glycidyl acrylate or methacrylate.

Preferably it is an epoxide resin, especially one containing at least one group of formula

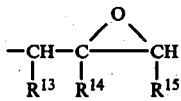

XVIII directly attached to an atom of oxygen, where either $R^{13}$ and $R^{15}$ each represents a hydrogen atom, in which case $R^{14}$ denotes a hydrogen atom or a methyl group, or $R^{13}$ and $R^{15}$ together represent $-CH_2CH_2-$, in which case $R^{14}$ denotes a hydrogen atom.

As examples of such resins may be mentioned polyglycidyl and poly(β-methylglycidyl) esters obtainable by reaction of a compound containing two or more carboxylic acid groups per molecule with epichlorohydrin, glycerol dichlorohydrin, or β-methylepichlorohydrin in the presence of an alkali. Such polyglycidyl esters may be derived from aliphatic polycarboxylic acids, e.g., succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid; and from aromatic polycarboxylic acids such as phthalic acid, isophthalic acid, and terephthalic acid. Other suitable polyglycidyl esters are obtainable by vinyl polymerisation of glycidyl esters of vinylic acids, especially glycidyl acrylate and glycidyl methacrylate.

Further examples are polyglycidyl and poly(β-methylglycidyl) ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These esters may be made from acyclic alcohols such as ethylene glycol, diethylene glycol, and higher poly(oxyethylene) glycols, propane-1,2-diol and poly(oxypropylene) glycols, propane-1,3-diol, poly(oxytetramethylene) glycols, pentane-1,5-diol, hexane-2,4,6-triol, glycerol, 1,1,1-trimethylolpropane, pentaerythritol, sorbitol, and poly(epichlorohydrin); from cycloaliphatic alcohols such as resorcitol, quinitol, bis(4-hydroxycyclohexyl)methane, 2,2-bis(4-hydroxycyclohexyl)propane, and 1,1-bis(hydroxymethyl)cyclohex-3-ene; and from alcohols having aromatic nuclei, such as N,N-bis(2-hydroxyethyl)aniline and p,p'-bis(2-hydroxyethylamino)diphenylmethane. Or they may be made from mononuclear phenols, such as resorcinol and hydroquinone, and from polynuclear phenols, such as bis(4-hydroxyphenyl)methane, 4,4'-dihydroxydiphenyl, bis(4-hydroxyphenyl)sulphone, 1,1,2,2-tetrakis(4-hydroxyphenyl)ethane, 2,2-bis(4-hydroxyphenyl)propane (otherwise known as bisphenol A), 2,2-bis(3,5-dibromo-4-hydroxyphenyl)propane, and novolaks formed from aldehydes such as formaldehyde, acetaldehyde, chloral, and furfuraldehyde, with phenol itself, and phenol substituted in the ring by chlorine atoms or by alkyl groups each containing up to nine carbon atoms, such as 4-chlorophenol, 2-methylphenol, and 4-tert.butylphenol.

Poly(N-glycidyl) compounds may also be used, e.g., N-glycidyl derivatives of amines such as aniline, n-butylamine, bis(4-aminophenyl)methane, and bis(4-methylaminophenyl)methane; triglycidyl isocyanurate; and N,N'-diglycidyl derivatives of cyclic alkylene ureas, such as ethyleneurea and 1,3-propyleneurea, and of hydantoins such as 5,5'-dimethylhydantoin. In general, however, they are not preferred.

Poly(S-glycidyl) compounds may also be used, e.g., di(S-glycidyl) derivatives of dithiols such as ethane-1,2-dithiol and bis(4-mercaptomethylphenyl) ether, but they also are not preferred.

Examples of epoxide resins having groups of formula XVIII where $R^{13}$ and $R^{15}$ conjointly denote a $-CH_2CH_2-$ group are bis(2,3-epoxycyclopentyl) ether, 2,3-epoxycyclopentyl glycidyl ether, and 1,2-bis(2,3-epoxycyclopentyloxy)ethane.

Epoxide resins having the 1,2-epoxide groups attached to different kinds of hetero atoms may be employed, e.g., the glycidyl ether-glycidyl ester of salicylic acid.

Epoxide resins in which some or all of the epoxide groups are not terminal may also be employed, such as vinylcyclohexene dioxide, limonene dioxide, dicyclopentadiene dioxide, 4-oxatetracyclo[6.2.1.0$^{2,7}$.0$^{3,5}$]undec-9-yl glycidyl ether, 1,2-bis(4-oxatetracyclo[6.2.1.0$^{2,7}$.0$^{3,5}$]undec-9-yloxy)ethane, 3,4-epoxycyclohexylmethyl 3',4'-epoxycyclohexanecarboxylate and its 6,6'-dimethyl derivative, ethylene glycol bis(3,4-epoxycyclohexanecarboxylate), 3-(3,4-epoxycyclohexyl)-8,9-epoxy-2,4-dioxaspiro-[5,5]undecane, and epoxidised butadienes or copolymers of butadiene with ethylenic compounds such as styrene and vinyl acetate.

If desired, a mixture of epoxide resins may be used.

Especially preferred epoxide resins used in this invention are diglycidyl ethers, which may have been advanced, of dihydric phenols such as 2,2-bis(4-hydroxyphenyl)propane and bis(4-hydroxyphenyl)methane and of dihydric aliphatic alcohols such as butane-1,4-diol.

If desired, the epoxide resin may be co-cured with a polyhydric alcohol, i.e., a compound having at least two alcoholic hydroxyl, preferably primary, groups per molecule. Preferably the polyhydric alcohol is present in a quantity sufficient to supply from 0.5 to 1.5, especially 0.75 to 1.25, alcoholic hydroxyl groups per 1,2-epoxide group of the epoxide resin. The polyhydric alcohol preferably contains, in addition to the alcoholic hydroxyl groups, only carbon, hydrogen, and, optionally, oxygen present as ether oxygen, acetal or carbonyloxy groups, and halogen atoms. It is further preferred that the polyhydric alcohol have a molecular weight of at least 100 and particularly more than 1000. Examples of suitable polyhydric alcohols are poly(oxyethylene) glycols, poly(oxypropylene) glycols, poly(oxytetramethylene) glycols, polyepichlorohydrins, poly(oxyethylene)-, poly(oxypropylene)-, and poly(oxytetramethylene) triols, obtainable by polymerisation of ethylene oxide, propylene oxide, or tetrahydrofuran in the presence of glycerol or 1,1,1-trimethylolpropane, hydroxyl-terminated polycaprolactones, copolymers of styrene with allyl alcohol, polyvinyl alcohols, hydroxypropylcellulose hydroxyl-containing polyvinyl acetals, and partial esters of cellulose, e.g., a cellulose acetate butyrate.

Vinyl monomers and prepolymers which may be polymerised include styrene, α-methylstyrene, allylbenzene, divinylbenzene, vinylcyclohexane, 4-vinylcyclohex-1-ene, N-vinylpyrrolidin-2-one, N-vinylcarbazole, acrolein, isoprene, butadiene, piperylene, vinyl acetate, and vinyl ethers such as isobutyl vinyl ether, methyl vinyl ether, trimethylolpropane trivinyl ether, glycerol trivinyl ether, vinyl ethers of ethylene glycol and poly(oxyethylene glycols), and cyclic vinyl ethers having at least two cyclic vinyl ether groups each forming part of a 3,4-dihydro-2H-pyran nucleus, such as 3,4-dihydro-2H-pyran-2-ylmethyl 3,4-dihydro-2H-pyran-2-carboxylate and its prepolymers. The preferred vinyl compounds are vinyl ethers of aliphatic monohydric alcohols and 3,4-dihydro-2H-pyran-2-ylmethyl 3,4-dihydro-2H-pyran-2-carboxylate and its prepolymers.

The aminoplasts preferred as component (a) contain, per molecule, at least two groups of formula —CH$_2$OR$^{16}$ directly attached to an amidic or thioamidic nitrogen atom or atoms, where R$^{16}$ denotes a hydrogen atom, an alkyl group of 1 to 4 carbon atoms, or an acetyl group. Examples of such aminoplasts are the N-hydroxymethyl, N-methoxymethyl, N-butoxymethyl, and N-acetoxymethyl derivatives of the following amides and amide-like substances.

1. Urea, thiourea, and the cyclic ureas having the formula

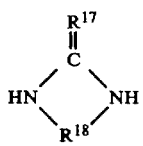

XIX in which
R$^{17}$ denotes oxygen or sulphur and
R$^{18}$ denotes either a group of formula,

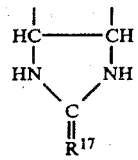

XX or a divalent group of 2 to 4 carbon atoms which may be substituted by methyl, methoxy, or hydroxy groups, and which may be interrupted by —CO—, —O—, or —N(R$^{19}$)—, where R$^{19}$ denotes an alkyl or hydroxyalkyl group containing up to 4 carbon atoms.

Examples of such cyclic ureas are ethyleneurea (imidazolidin-2-one), dihydroxyethyleneurea (4,5-dihydroxyimidazolidin-2-one), hydantoin, uron (tetrahydrooxadiazin-4-one), 1,2-propyleneurea (4-methylimidazolidin-2-one), 1,3-propyleneurea (hexahydro-2H-pyrimid-2-one), hydroxypropyleneurea (5-hydroxyhexahydro-2H-pyrimid-2-one), dimethylpropyleneurea (5,5-dimethylhexahydro-2H-pyrimid-2-one), dimethylhydroxypropyleneurea and dimethylmethoxypropyleneurea (4-hydroxy- and 4-methoxy-5,5-dimethylhexahydro-2H-pyrimid-2-one), 5-ethyltriazin-2-one, and 5-(2-hydroxyethyl)-triazin-2-one.

II. Carbamates and dicarbamates of aliphatic monohydric and dihydric alcohols containing up to four carbon atoms, e.g., methyl, ethyl, isopropyl, 2-hydroxyethyl, 2-methoxyethyl, 2-hydroxy-n-propyl and 3-hydroxy-n-propyl carbamates, and ethylene and 1,4-butylene dicarbamates.

III. Melamine and other polyamino-1,3-triazines such as acetoguanamine, benzoguanamine, and adipoguanamine.

If desired, aminoplasts containing both N-hydroxymethyl and N-alkoxymethyl, or N-hydroxymethyl and N-acetoxymethyl, groups may be used (for example, a hexamethylolmelamine in which 1 to 3 of the hydroxyl groups have been etherified with methyl groups).

The preferred aminoplasts are condensation products of urea, uron, hydantoin, or melamine with formaldehyde, and the partially or fully etherified products of such condensation products with an aliphatic monohydric alcohol of 1 to 4 carbon atoms.

The preferred phenoplasts are resols made from a phenol and an aldehyde. Suitable phenols include phenol itself, resorcinol, 2,2-bis(p-hydroxyphenyl)propane, p-chlorophenol, a phenol substituted by one or two alkyl groups, each of 1 to 9 carbon atoms, such as o-, m-, and p-cresol, the xylenols, p-tertiary butylphenol, p-nonylphenol, and phenyl-substituted phenols, especially p-phenylphenol. The aldehyde which is condensed with the phenol is preferably formaldehyde, but other aldehydes such as acetaldehyde and furfuraldehyde may also be used. If desired, a mixture of such curable phenol-aldehyde resins may be used.

The preferred resols are condensation products of phenol, p-chlorophenol, resorcinol, or o-, m-, or p-cresol with formaldehyde.

Preferably the compositions of this invention, when they are to be photopolymerised, also contain a sensitiser. We have found that, by incorporation of suitable sensitisers, the speed of curing is yet further increased, thereby permitting the use of even shorter exposure times and/or of less powerful sources of irradiation. Further, the sensitivity to visible light is enhanced. Sensitisers other than dyes have been found the more effective, particularly aromatic polycyclic compounds having at least three fused benzene rings and having an ionisation energy of less than about 7.5 ev. Suitable such sensitisers are described in U.S. Pat. No. 4,069,054, and include anthracene, rubrene, perylene, phenanthrene, fluoranthene, and pyrene. We prefer to include from 0.1 to 2%, and especially from 0.25 to 0.75%, by weight of the sensitiser, calculated on the weight of (a).

In the photopolymerising step actinic radiation of wavelength from 200 to 600 nm is preferably used. Suitable sources of actinic radiation include carbon arcs, mercury vapour arcs, fluorescent lamps with phosphors emitting ultraviolet light, argon and xenon glow lamps, tungsten lamps, and photographic flood lamps. Of these, mercury vapour arcs, particularly sun lamps, fluorescent sun lamps, and metal halide lamps are most suitable. The time required for the exposure will depend upon a variety of factors which include, for example, the individual polymerisable substrate used, the type of light source, and its distance from the irradiated material. Suitable times may be readily determined by those familiar with photopolymerisation techniques. If, as in the process described below, it is necessary that the product so photopolymerised must still be curable on heating with the heat-curing agent admixed therewith, then, of course, irradiation is carried out at a temperature below that at which substantial heat-curing of the photopolymerised product by means of that heat-curing agent would occur.

When the compositions of this invention are to be polymerised substantially by means of heat alone, they are preferably heated to a temperature of from 100° C. to 175° C., and preferably for from 3 to 30 minutes.

The compositions of this invention may be used as surface coatings. They may be applied to a substrate such as steel, aluminium, copper, cadmium, zinc, paper, or wood, preferably as a liquid, and irradiated or heated. By photopolymerising part of the coating, as by irradiation through a mask, those sections which have not been exposed may be washed with a solvent to remove the unpolymerised portions while leaving the photopolymerised, insoluble portions in place. Thus the compositions of this invention may be used in the production of printing plates and printed circuits. Methods of producing printing plates and printed circuits from photopolymerisable compositions are well known (see, e.g., British Pat. No. 1,495,746).

The compositions may also be used as adhesives. A layer of the composition may be sandwiched between two surfaces of objects, then the assembly is heated, or irradiated and, if desired, heated to complete the polymerisation. When photopolymerisation is to be employed it is, of course, necessary that at least one of the objects be transparent to the actinic radiation, e.g., of glass.

The compositions are also useful in the production of fibre-reinforced composites, including sheet moulding compounds.

They may be applied directly, continuously or batchwise, in liquid form, to reinforcing fibres (including strands, filaments, and whiskers), which may be in the form of woven or nonwoven cloth, unidirectional lengths, or chopped strands, especially glass, boron, stainless steel, tungsten, alumina, silicon carbide, asbestos, potassium titanate whiskers, an aromatic polyamide such as poly(m-phenylene isophthalamide), poly(p-phenylene terephthalamide), or poly(p-benzamide), polyethylene, polypropylene, or carbon.

The fibre-reinforced composite may also be made from films of the photopolymerised composition, by a batch process or continuously. In the batch process the fibrous reinforcing material is laid on a film of the photopolymerised composition which is advantageously under slight tension, when a second such film may, if desired, be laid on top, and then the assembly is pressed while being heated. It may also be made continuously, such as by contacting the fibrous reinforcing material with a film of the photopolymerised composition, then, if desired, placing a second such film on the reverse face of the fibrous reinforcing material and applying heat and pressure. More conveniently, two such films, preferably supported on the reverse side by belts or strippable sheets, are applied simultaneously to the fibrous reinforcing material so as to contact each exposed face. When two such films are applied, they may be the same or different.

Multilayer composites may be made by heating under pressure interleaved films and layers of one or more fibrous reinforcing materials. When unidirectional fibres are used as the reinforcement material, successive layers of them may be oriented to form crossply structures.

With the fibrous reinforcing material there may be used additional types of reinforcement such as a foil of metal (e.g., aluminium, steel, or titanium) or a sheet of a plastics material (e.g., an aromatic or aliphatic polyamide, a polyimide, a polysulphone, or a polycarbonate) or of a rubber (e.g., a neoprene or acrylonitrile rubber).

Alternatively, a mixture of the reinforcing fibers and a composition of this invention is heated to form a composite directly.

In the production of sheet moulding compounds, a composition of this invention, together with the chopped strand reinforcing material and any other components, is exposed to irradiation in layers through supporting sheets or is heated.

The polymerisable composition is preferably applied so that the composite contains a total of from 20 to 80% by weight of the said composition and, correspondingly, 80 to 20% by weight of the reinforcement. More preferably, a total of 30 to 50% by weight of the composition is employed.

The compositions of this invention are useful in the production of putties and fillers. They may be used as dip-coatings, an article to be coated being dipped in the liquid composition, withdrawn, and the adhering coating being heated, or being irradiated to photopolymerise (and hence solidify it) and subsequently, if desired, being heated.

We have found that it is possible, using the salts of formula VI, to cure epoxide resins and phenoplasts in two stages; the resin is first converted into the partially cured B-stage by exposing it to actinic radiation in the presence of the sulphoxonium salt and a latent, heat-activated crosslinking agent for the epoxide resin or phenoplast, and, in a second stage, the partially cured composition is heated so that curing is completed by means of the heat-activated crosslinking agent. Thus, a liquid or semiliquid composition may be prepared, which may then be shaped or used to impregnate a substrate while being irradiated to solidify it; then the solidified body is heated when desired, to complete the cure of the resin.

According, therefore, to another embodiment of this invention, an epoxide resin or a phenoplast is irradiated in the presence of an amount of a sulphoxonium salt of formula VI effective for the polymerisation of the epoxide resin or phenoplast and of a curing amount of a latent heat-curing agent for the epoxide resin or phenoplast to form a B-stage product, and, when desired, curing of the composition is completed by heating it.

A further embodiment comprises a composition containing an epoxide resin or a phenoplst, an amount of a sulphoxonium salt of formula VI effective for polymerisation of the said epoxide resin or phenoplast on exposure of the composition to actinic radiation, and a curing amount of a latent heat-curing agent for the epoxide resin or phenoplast.

Suitable heat-activated crosslinking agents for the epoxide resin compositions include polycarboxylic acid anhydrides, complexes of amines, especially primary or tertiary aliphatic amines such as ethylamine, trimethylamine, and n-octyldimethylamine, with boron trifluoride or boron trichloride, and latent boron difluoride chelates. Aromatic polyamines and imidazoles are usually not preferred, because indifferent results are obtained, possibly due to reaction between the acid catalyst liberated and the amine. Dicyandiamide can be used successfully, providing it is in relatively coarse particles.

Suitable heat-activated crosslinking agents for resols include hexamethylenetetramine and paraform.

The temperature and duration of heating required for the thermal curing after photopolymerisation, and the proportions of heat-activated curing agent, are readily found by routine experimentation and easily derivable from what is already well known concerning the heat-curing of epoxide resins and phenol-aldehyde resols.

Compositions containing resins having epoxide groups or phenolic hydroxyl groups through which they can be heat-cured after photopolymerisation are particularly useful in the production of multilayer printed circuits.

Conventionally, a multilayer printed circuit is prepared from several double-sided printed circuit boards of copper, stacked one on top of another and separated from each other by insulating sheets, usually of glass fibre impregnated with an epoxide resin or a phenol-formaldehyde resin in the B-stage. If a heat-curing agent is not admixed with the layer of photopolymerisable resin in the circuit board, it can be incorporated in the insulating layers which alternate with the plates, these layers conveniently being of an epoxide resin or phenol-formaldehyde resin prepreg; sufficient of the heat-curing agent contained in the prepreg, providing the latter is not too thick, migrates to induce crosslinking of the photopolymerised epoxide resin or phenol-formaldehyde resin. The stack is heated and compressed to bond the layers together. Conventional photopolymerisable materials, however, do not form strong bonds either with copper or with resin-impregnated glass fibre sheets. A stack which is bonded with the photopolymer still covering the copper is therefore inherently weak and in use can become delaminated. It is therefore normal practice to remove the residual photopolymer after the etching stage, either by means of powerful solvents or by a mechanical method, e.g., by means of brushes. Such a stripping process can damage the copper of the printed circuit or the surface of the laminate on which the circuit rests, and so there is a need for a method which would avoid the necessity of removing the photopolymerised material prior to bonding the boards together. The presence of residual crosslinking groups in the compositions of this invention means that crosslinking can occur when the boards are bonded, resulting in good adhesion to the copper and to the resin-impregnated glass fibre substrate, so avoiding the necessity just referred to; also, products with a higher glass transition temperature are obtained.

Another application involving heat-curing after photopolymerisation of the compositions of this invention is in filament winding. Thus, a continuous tow of fibrous reinforcement is impregnated with a composition containing a latent heat-curing agent and then wound around a mandrel or former while exposing the winding to actinic radiation. Such filament windings still have a degree of flexibility, permitting the mandrel or former to be removed more readily than when a rigid winding is formed in one step. When required, the winding is heated to crosslink the composition.

In a further such application, a layer of the composition in liquid form is irradiated until it solidifies, producing a film adhesive, which is then placed between, and in contact with, two surfaces which are to be bonded together, and the assembly is heated to complete crosslinking of the composition. The film may be provided on one face with a strippable backing sheet, e.g., of a polyolefin or a polyester, or of cellulosic paper having a coating of a silicone release agent. Manipulation of the assembly is often easier if the film has a tacky surface. This may be produced by coating the film with a substance which is tacky at room temperature but which crosslinks to a hard, insoluble, infusible resin under the conditions of heat employed to complete crosslinking of the composition. However, an adequate degree of tackiness often exists without additional treatment, especially if polymerisation of the composition has not proceeded too far. Suitable adherends include metals such as iron, zinc, copper, nickel, and aluminium, ceramics, glass, and rubbers.

The following Examples illustrate the invention. Unless otherwise indicated, parts are by weight.

Examples 1 to 4 illustrate the preparation of sulphoxonium salts of this invention.

EXAMPLE 1

Preparation of Dimethyl-p-toluenesulphonylmethylsulphoxonium hexafluorophosphate Dimethylsulphoxonium methylide was prepared by the method described by Corey and Chaykovsky, loc. cit., from trimethylsulphoxonium chloride (25.7 parts) by treatment with sodium hydride (6.7 parts) in dry tetrahydrofuran. This ylide was converted into dimethylsulphoxonium p-toluenesulphonylmethylide by reaction with p-toluenesulphonyl fluoride (17.4 parts) using the method described by Truce and Madding, loc. cit. The toluenesulphonylmethylide was neutralised by the addition of 65% aqueous hexafluorophosphoric acid (49.5 parts) over 15 minutes, followed by concentration of the solution. The white solid which precipitated was filtered off, washed with water, and dried under vacuum to give 20 parts of the desired product (VI, $R=p-CH_3C_6H_4$, $R^6=H$, $R^7=R^8=CH_3$, $q=t=1$, $Z^{t-}=PF_6^-$), mpt. 174°–5° C.; NMR (acetone -$d_6$) 2.50 (s-3H), 4.23 (s-6H), 6.20 (s-2H), 7.5–8.2 (m-4H); IR (KBr disc) 3020, 3000, 2930, 2920, 1590, 1400, 1330, 1300, 1250, 1160, 1030, 940, 840, 750 cm$^{-1}$; UV (ethanol) $\lambda_{max}$ 255 nm (data for product recrystallised from methanol).

EXAMPLE 2

Preparation of Dimethylphenylsulphonylmethylsulphoxonium hexafluorophosphate Dimethylsulphoxonium methylide was prepared as described in the previous Example. This ylide was converted into dimethylsulphoxonium benzenesulphonylmethylide by reaction with benzenesulphonyl fluoride (20 parts) using the method described by Truce and Madding, loc. cit. The benzenesulphonylmethylide was neutralised by the addition of 65% aqueous hexafluorophosphoric acid (49.5 parts), followed by concentration of the solution. The white solid which precipitated was filtered off, washed with water and dried under vacuum to give 23 parts of the desired product (VI, R=$C_6H_5$, $R^6$=H, $R^7$=$R^8$=$CH_3$, t=q=1, $Z^{t-}$=$PF_6^-$), m.pt. 135°–7° C.; NMR (acetone-$d_6$) 4.23 (s-6H), 6.0 (s-2H), 7.7–8.2 (m-5H); IR (KBr disc) 3020, 3000, 2930, 1610, 1450, 1350, 1330, 1240, 1160, 1080, 1030, 840, 750 cm$^{-1}$; UV (ethanol) $\lambda_{max}$ 257 nm (data for product recrystallised from methanol).

EXAMPLE 3

Preparation of Dimethyl-p-toluenesulphonylmethylsulphoxonium hexafluoroantimonate A further portion of the toluenesulphonylmethylide (2.46 g) prepared previously was dissolved in 20 ml of 0.5 M hydrochloric acid, sodium hexafluoroantimonate (2.6 g) was added with stirring, and the mixture was stirred for a further 30 minutes. The desired hexafluoroantimonate (VI, R=p—$CH_3C_6H_4$, $R^6$=H, $R^7$=$R^8$=$CH_3$, q=t=1, $Z^{t-}$=$SbF_6$) was filtered off and dried in vacuo. Yield: 1.9 g.

EXAMPLE 4

Preparation of Tris(dimethyl-p-toluenesulphonylmethylsulphoxonium)orthophosphate To a solution of a further 2.46 g of the toluenesulphonylmethylide in 20 ml of 0.5 M hydrochloric acid was added with stirring 1.40 g of silver phosphate. The precipitated silver chloride was filtered off and the filtrate was allowed to stand overnight. The desired phosphate (VI, R=p—$CH_3C_6H_4$, $R^6$=H, $R^7$=$R^8$=$CH_3$, q=1, t=3, $Z^{t-}$=$PO_4^{---}$) separated out as colourless crystals.

EXAMPLE 5

Mixtures each containing 96 parts of 2,2-bis(p-glycidyloxyphenyl)propane and 4 parts of either dimethyl-p-toluenesulphonylmethylsulphoxonium hexafluorophosphate or the corresponding hexafluoroantimonate were applied as films 10 μm thick on tinplate. The films were exposed to radiation from a medium pressure mercury arc lamp (80 w per cm) at a distance of 8 cm. In each case a tack-free, solvent-resistant coating was obtained after 10 seconds.

EXAMPLE 6

A composition comprising 98.7 parts of 2,2-bis(p-glycidyloxyphenyl)propane and 1.3 parts of dimethyl-p-toluenesulphonylmethylsulphoxonium hexafluorophosphate was applied as a film 10 μm thick on tinplate and heated at 150° C. for 20 minutes without exposure to radiation. A hard, tack-free coating was obtained.

EXAMPLE 7

A mixture of 96 parts of 3,4-epoxycyclohexyl 3,4-epoxycyclohexanecarboxylate and 4 parts of dimethyl-p-toluenesulphonylmethylsulphoxonium hexafluorophosphate was applied as a film 10 μm thick to tinplate. Irradiation of the film under the conditions described in Example 5 for 5 seconds gave a tack-free coating.

EXAMPLE 8

A composition comprising 96 parts of a commercially-available phenol-formaldehyde resol having a P:F molar ratio of 1:1.6 and 4 parts of dimethyl-p-toluenesulphonylmethylsulphoxonium hexafluorophosphate was applied as a film 10 μm thick on tinplate and irradiated as described in Example 5. A tack-free coating was obtained after 10 seconds.

EXAMPLE 9

The procedure of Example 8 was repeated, using in place of the resol a commercially available urea-formaldehyde resin having a U:F ratio of 1:1.4. A tack-free coating was obtained after irradiation for 5 seconds.

EXAMPLE 10

A mixture of 96 parts of a commercially available methylated melamine-formaldehyde resin (substantially hexamethoxymethylmelamine) and 4 parts of dimethyl-p-toluenesulphonylmethylsulphoxonium hexafluorophosphate was applied as a film 10 μm thick on tinplate. The film was irradiated for 30 seconds under the conditions described in Example 5 and then heated for 15 minutes at 120° C. A highly solvent-resistant coating was obtained.

EXAMPLE 11

A composition comprising 97 parts of 2,2-bis(p-glycidyloxyphenyl)propane and 3 parts of dimethylphenylsulphonymethylsulphoxonium hexafluorophosphate was applied as a film 10 μm thick on tinplate and irradiated as described in Example 5. A tack-free coating was obtained after 20 seconds.

EXAMPLE 12

Tris(dimethyl-p-toluenesulphonylmethylsulphoxonium)orthophosphate (3 parts) was dissolved in 10 parts of the urea-formaldehyde resin used in Example 9, and a coating 10 μm thick of the solution on tinplate was irradiated for 10 seconds as described in Example 5, a tack-free coating being obtained.

What is claimed is:

1. A polymerizable composition which comprises
    (a) a compound, or mixture of compounds, capable of being transformed into a higher-molecular weight material under the influence of a cationic catalyst,
    (b) an effective amount of an aromatic sulfonylsulfoxonium salt of the formula

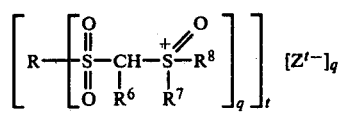

VI where q is an integer of from 1 to 4,

R denotes an aliphatic, cycloaliphatic or aromatic group of valency q, having from 1 to 25 carbon atoms and being directly linked through a carbon atom thereof to the sulfur atom of the indicated adjacent sulfonyl group, $R^6$ denotes a hydrogen atom, an alkyl or aralkyl group of 1 to 25 carbon atoms, an acyl group of formula $-COR^9$ or a group of formula $$-CO-NH-(CO)_r-R^{10} \qquad \text{VII}$$

or $$\underset{\underset{O}{\|}}{\overset{\overset{O}{\|}}{-S-R^{11}}} \qquad \text{VIII}$$

one, but not both, of R and $R^6$ denoting a homocyclic aromatic group of 6 to 25 carbon atoms or a heterocyclic aromatic group of 4 to 25 carbon atoms containing one or more nitrogen, oxygen or sulfur atoms in the aromatic ring, $R^7$ denotes an alkyl group of 1 to 12 carbon atoms, an alkenyl group of 2 to 6 carbon atoms, a cycloalkyl group of 3 to 8 carbon atoms, a cycloalkylalkyl group of 4 to 10 carbon atoms, an aryl group of 6 to 24 carbon atoms, or an aralkyl group of 7 to 16 carbon atoms, $R^8$ has the same meaning as $R^7$, or $R^8$ is a dialkylamino group of 2 to 6 carbon atoms, or if $R^7$ is alkyl of 1 to 12 carbon atoms, $R^8$ may also be an arylamino group of 6 to 8 carbon atoms, $R^9$ denotes an alkyl, aryl, or aralkyl radical of 1 to 25 carbon atoms, directly linked through a carbon atom thereof to the indicated —CO— group, r is zero or 1, $R^{10}$ denotes an alkyl, aryl, or aralkyl radical of 1 to 25 carbon atoms, directly linked through a carbon atom thereof to, if r denotes zero, the indicated nitrogen atom, or if r denotes 1, the carbon atom of the indicated adjacent carbonyl group, $R^{11}$ denotes an alkyl, aryl, or aralkyl radical of 1 to 25 carbon atoms, directly linked through a carbon atom thereof to the indicated sulfur atom, t represents 1, 2, or 3, and $Z^{t-}$ denotes a t-valent anion of a protic acid.

2. A composition according to claim 1, in which R represents a monocyclic or dicyclic homocyclic aryl or aralkyl group of 6 to 16 carbon atoms.

3. A composition according to claim 1, in which R represents a monocyclic or dicyclic arylene or aralkylene group of 6 to 16 carbon atoms.

4. A composition according to claim 1, in which $R^7$ and $R^8$ are each an alkyl group of 1 to 4 carbon atoms, a phenyl group, a naphthyl group, or a phenyl or a naphthyl group substituted in the aromatic ring or rings by one or two alkyl groups, each of 1 to 4 carbon atoms, or by one or two alkoxy groups, each of 1 to 4 carbon atoms, or by one or two fluorine, chlorine, or bromine atoms.

5. A composition according to claim 1, in which R denotes an aromatic group and $R^9$ denotes an aliphatic radical of 1 to 8 carbon atoms.

6. A composition according to claim 1, in which R denotes an aromatic group and $R^{10}$ denotes an aliphatic radical of 1 to 8 carbon atoms.

7. A composition according to claim 1, in which R denotes an aromatic group and $R^{11}$ denotes an aliphatic radical of 1 to 8 carbon atoms.

8. A composition according to claim 1, wherein $Z^{t-}$ denotes an anion of an inorganic acid.

9. A composition according to claim 1, where $Z^{t-}$ denotes $Cl^-$, $Br^-$, $NO_3^-$, $HSO_4^-$, $HSO_3^-$, $ClO_4^-$, $CF_3SO_3^-$, $CF_3COO^-$, $CH_3C_6H_4SO_3^-$, $H_2PO_4^-$, $SO_4^{--}$, $PO_4^{---}$, $SbF_5(OH)^-$, or an anion of formula $$MX_n^- \qquad \text{XI}$$

where
M denotes an atom of antimony, bismuth, boron, arsenic, or phosphorus,
X denotes a fluorine or chlorine atom, and
n is 4, 5, or 6 and is one more than the valency of m.

10. A composition according to claim 1, in which (b) is dimethyl-p-toluenesulfonylmethylsulfoxonium hexafluorophosphate, dimethyltoluene-p-sulfonylmethylsulfoxonium hexafluoroantimonate, tris(dimethyltoluene-p-sulfonylmethylsulfoxonium)orthophosphate, or dimethylphenylsulfonylmethylsulfoxonium hexafluorophosphate.

11. A composition according to claim 1, wherein (a) is a 1,2-epoxide, a vinyl monomer or prepolymer, an aminoplast, or a phenoplast.

12. A composition according to claim 1, wherein (a) is either an epoxide resin or a resol made from a phenol and an aldehyde.

13. A composition according to claim 1, containing 0.1 to 7.5 parts by weight of (b) per 100 parts by weight of (a).

14. A composition according to claim 12, which also contains a curing amount of a latent heat-curing agent for epoxide resins or resol resins.

* * * * *